(12) United States Patent
Kim

(10) Patent No.: US 12,740,761 B2
(45) Date of Patent: Sep. 22, 2026

(54) MEDICAL CONDOM AND AUTOMATIC MEDICAL CONDOM SUPPLY DEVICE

(71) Applicant: IBMsol Co., Ltd., Seoul (KR)

(72) Inventor: Hee Kyung Kim, Seoul (KR)

(73) Assignee: IBMsol Co., Ltd., Seoul (KR)

( * ) Notice: Subject to any disclaimer, the term of this patent is extended or adjusted under 35 U.S.C. 154(b) by 459 days.

(21) Appl. No.: 18/330,218

(22) Filed: Jun. 6, 2023

(65) Prior Publication Data

US 2023/0329672 A1 Oct. 19, 2023

Related U.S. Application Data

(63) Continuation of application No. PCT/KR2021/010545, filed on Aug. 10, 2021.

(30) Foreign Application Priority Data

Dec. 7, 2020 (KR) ........................ 10-2020-0169536

(51) Int. Cl.
*A61B 8/00* (2006.01)
*A61B 8/12* (2006.01)
(Continued)

(52) U.S. Cl.
CPC .............. *A61B 8/4422* (2013.01); *A61B 8/12* (2013.01); *A61B 46/17* (2016.02); *A61B 50/30* (2016.02); *A61B 2050/3013* (2016.02)

(58) Field of Classification Search
CPC .......... B65D 83/08; B65D 3/00; A61B 46/10; A61B 50/20; A61B 30/20; A61B 7/02;
(Continued)

(56) References Cited

U.S. PATENT DOCUMENTS 3,747,298 A * 7/1973 Lieberman .......... B65B 67/1266 53/384.1
5,000,344 A * 3/1991 Janssen ..................... A47F 1/08 221/92
(Continued)

FOREIGN PATENT DOCUMENTS

CN 202397515 U 8/2012
EP 3011939 A1 4/2016
(Continued)

OTHER PUBLICATIONS

Office Action dated Dec. 29, 2025, issued in counterpart Chinese patent application No. 202180092415.4 with English translation (18 pages).

*Primary Examiner* — Rakesh Kumar
(74) *Attorney, Agent, or Firm* — WHDA, LLP

(57) ABSTRACT

An automatic medical condom supply device includes a condom supply part installed inside a device body to supply, one by one, medical condom modules each of which is wrapped in a wrapper, a condom withdrawal part moving, to the outside of the device body, through an outlet formed in the device body, each of the medical condom modules supplied from the condom supply part, a wrapper removal part removing the wrapper of the medical condom module withdrawn to the outside of the device body by the condom withdrawal part, and a condom holding part installed outside the device body to hold a medical condom discharged through the outlet so that a medical probe is coupled with the medical condom from which the wrapper has been removed.

12 Claims, 12 Drawing Sheets

(51) Int. Cl.
*A61B 46/17* (2016.01)
*A61B 50/30* (2016.01)

(58) Field of Classification Search
CPC ...... B65H 18/00; B65H 83/00; B65H 18/145; B65H 37/002
USPC ...................................... 422/300; 221/9, 208
See application file for complete search history.

(56) References Cited

U.S. PATENT DOCUMENTS 5,466,897 A * 11/1995 Ross ...................... A61B 50/30 221/266
5,511,689 A * 4/1996 Frank .................... A61F 15/002 206/440
5,806,278 A 9/1998 Shelledy
5,975,083 A * 11/1999 Henderson, Jr. ..... A41D 13/082 128/878
6,018,835 A * 2/2000 Schonfeld ................ B08B 3/02 15/97.1
6,643,998 B1 * 11/2003 Curtis ...................... B65B 9/13 53/434
7,117,971 B1 * 10/2006 Cornacchia ............. A61B 7/02 221/266
7,246,720 B1 7/2007 Montoya, Jr.
9,675,721 B2 * 6/2017 Dayton ..................... A61L 2/10
9,861,514 B2 * 1/2018 Chan ....................... A61F 6/005
2002/0170771 A1 * 11/2002 Milam ..................... A61B 7/02 181/131
2006/0186131 A1 * 8/2006 Panning ................. A47K 10/16 221/63
2006/0201960 A1 * 9/2006 Frayne ................. B65D 81/052 221/45
2008/0061073 A1 * 3/2008 Laroche ............... A47K 10/426 221/63
2008/0222929 A1 * 9/2008 Sawin .................. A47K 10/421 221/45
2008/0223868 A1 * 9/2008 Sawin .................. B65D 75/545 221/63
2008/0264805 A1 10/2008 Felitsyn
2010/0212995 A1 * 8/2010 Hmayakyan ............. A61B 7/02 181/131
2011/0101029 A1 * 5/2011 Lewis, II ............ A47K 5/1202 222/325
2011/0186589 A1 * 8/2011 Lee ....................... A61B 42/50 221/36
2011/0186590 A1 * 8/2011 Lee ....................... A61B 50/30 600/528
2012/0261593 A1 * 10/2012 Noori ....................... A61L 2/10 250/492.1
2013/0108507 A1 * 5/2013 Reiseneder ............ A61B 46/10 422/28
2015/0128997 A1 * 5/2015 Lesic ........................ B08B 1/30 15/210.1
2015/0136896 A1 * 5/2015 Beebe ...................... H05K 5/03 428/80
2015/0360897 A1 * 12/2015 Bekavac .............. B65D 33/002 312/35
2016/0074208 A1 * 3/2016 Chan ....................... A61F 6/005 225/32
2017/0049954 A1 * 2/2017 Edwards ................. A61M 5/19
2017/0258435 A1 * 9/2017 Fishberger ............... A61B 7/02
2018/0221103 A1 * 8/2018 Bayasi ..................... A61B 7/02
2019/0218018 A1 * 7/2019 Umentum .......... B65D 83/0805
2020/0138539 A1 * 5/2020 Perlman ................... A61B 7/00

FOREIGN PATENT DOCUMENTS

GB 2531617 A * 4/2016 ............. A61F 6/005
JP H06-237904 A 8/1994
JP 2011072511 A * 4/2011 ............... A61B 8/00
JP 2012115551 A * 6/2012 ............... A61B 8/00
KR 20-1995-0010903 U 5/1995
KR 10-2016-0038557 A 4/2016
KR 20160038557 A * 4/2016 ............. A61B 17/04
KR 10-2020-0058310 A 5/2020
KR 20200058310 A * 5/2020 ........... A61B 8/4422
WO 2012/141672 A2 10/2012
WO 2016/052946 A1 4/2016

* cited by examiner 110
111
113
300
333
331
130
433
330
320
310
311
313
321
200
210
221
223
220
430
431c
431b
421
420
423
400
410
10
120
123
125
121
510
511
513
520
431a
500
30

Ⅱ－Ⅱ

Ⅲ—Ⅲ

MEDICAL CONDOM AND AUTOMATIC MEDICAL CONDOM SUPPLY DEVICE

CROSS-REFERENCE TO RELATED APPLICATIONS

This application is a Continuation of International Application No. PCT/KR2021/010545 filed on Aug. 10, 2021, which claims priority from Korean Application No. 10-2020-0169536 filed on Dec. 7, 2020. The aforementioned applications are incorporated herein by reference in their entireties.

TECHNICAL FIELD

The present disclosure relates generally to a medical condom and an automatic medical condom supply device. More particularly, the present disclosure relates to a medical condom that is put in a non-contact manner on a medical probe used for ultrasound examination in obstetrics and gynecology, and to an automatic medical condom supply device that can automatically supply a medical condom by removing a wrapper of a medical condom module.

RELATED ART

In general, ultrasound examination is a process for diagnosing the presence or absence of diseases in organs inside the human body using harmless ultrasound waves, and is used in various medical fields because the examination is relatively inexpensive, simple, and safe (non-radiation). In Korea, the number of ultrasound examinations has been rapidly increasing due to national health insurance coverage.

Since ultrasound probes come into contact with an unspecified number of patients during the examination, various pathogens exist on the probe when the probes do not undergo periodic sterilization after the examination. In addition, since the probe is held by the user's hand during the examination, it can become a breeding ground for pathogens when proper hand hygiene is neglected by the user.

In particular, in the case of a vaginal ultrasound probe used in obstetrics and gynecology, it is inserted into the patient's vaginal cavity and comes into direct contact with the vaginal mucosa and cervix. Therefore, contamination of the probe can cause not only various sexually transmitted infections but also human papillomavirus (HPV) infection, which is the cause of cervical cancer. For this reason, the vaginal ultrasound probe is considered a semi-critical medical device and requires high-level sterilization before the examination.

In obstetrics and gynecology, ultrasound examination is performed in the following manner. The probe is primarily sterilized before the examination, and then a disposable protective cover (condom) is put on the sterilized probe. This process has to be repeated for each patient before the examination.

However, there are frequent cases where the primarily sterilized probe is recontaminated during the process of putting the cover on the probe. The primarily sterilized probe is inserted into the patient's vaginal cavity after being covered with a sterilized condom. Since the user manually puts the condom on the probe while wearing sterilized gloves, the sterilized gloves are inevitably contaminated in the preceding process of removing a wrapper (non-sterile state). As a result, the condom in the wrapper is contaminated, so the previous sterilization process becomes meaningless due to contamination at the final stage.

In addition, since the user needs to directly remove the condom wrapper and put the condom on the probe while holding the condom, it takes a long time to prepare for the examination, thereby delaying the patient's waiting time for the examination.

SUMMARY

Accordingly, the present disclosure has been made keeping in mind the above problems occurring in the related art, and an objective of the present disclosure is to provide a medical condom that allows a user to automatically couple the medical condom to a medical probe without contact with the medical condom, and an automatic medical condom supply device that can automatically supply a medical condom by separating the medical condom from a wrapper.

In order to accomplish the above objective, according to one aspect of the present disclosure, there is provided an automatic medical condom supply device including: a device body; a condom supply part installed inside the device body and configured to supply, one by one, medical condom modules each of which is wrapped in a wrapper; a condom withdrawal part configured to move, to an outside of the device body, through an outlet formed in the device body, each of the medical condom modules supplied from the condom supply part; a wrapper removal part configured to remove the wrapper of the medical condom module withdrawn to the outside of the device body by the condom withdrawal part; and a condom holding part installed outside the device body and configured to hold a medical condom discharged through the outlet so that a medical probe is coupled with the medical condom from which the wrapper has been removed.

With this configuration, the medical condom may be automatically supplied by peeling off the wrapper.

Here, the condom withdrawal part may include: a guide member installed inside the device body and configured to guide the condom module supplied from the condom supply part to be moved toward the outlet; a transfer member configured to withdraw the condom module loaded on the guide member out of the outlet via a wrapper removal position; and a transfer member driver configured to reciprocally drive the transfer member.

With this configuration, the medical condom modules supplied one by one may be automatically withdrawn and supplied to the outside of the device body.

In addition, the guide member may include: a bottom guide portion configured to support the condom module to be slidably moved in a seated state on the bottom guide portion; and a side guide portion formed by bending at an edge of the bottom guide portion.

With this configuration, the condom module may be guided to pass through the wrapper removal position.

In addition, the transfer member may include a push member installed inside the device body to be reciprocally movable, and configured to be moved while pushing the condom module supplied from the condom supply part and loaded on the guide member out of the outlet via the wrapper removal position by the wrapper removal part.

With this configuration, the medical condom module may be withdrawn by easily removing the wrapper.

In addition, the wrapper removal part may include: a laser generation module installed inside the device body and configured to partially cut the wrapper of the condom module using a laser; and a wrapper clamping member installed on a movement path of the condom module and configured to forcibly peel off the wrapper partially cut by the laser generation module.

With this configuration, the wrapper of the medical condom module may be automatically removed.

In addition, the wrapper clamping member may include a pair of wrapper clamping members that are symmetrically disposed on opposite sides of the outlet, and each of the pair of wrapper clamping members may include upper and lower clamping members vertically installed to face each other and be spaced apart from each other and configured to vertically interfere with an edge of the wrapper of the condom module to separate the wrapper from the medical condom moved through the outlet.

In addition, each of the upper and lower clamping members may have a friction protrusion on an end portion thereof that interferes with the wrapper.

With this configuration, the wrapper of the medical condom module may be easily separated and removed.

In addition, at least one of the upper and lower clamping members may be installed to be reciprocally movable.

With this configuration, the wrapper of the medical condom module may be firmly clamped and securely separated from the medical condom module.

In addition, the condom holding part may include: a guide bracket installed outside the outlet of the device body and configured to support an edge of the medical condom discharged through the outlet and guide movement of the medical condom; and a condom support member installed at a front end of the guide bracket and configured to support the edge of the medical condom so that the medical probe is coupled with the medical condom.

With this configuration, the medical condom from which the wrapper has been removed may be safely held so that the medical condom is coupled with a medical probe medical probe for obstetrics and gynecology without holding the medical condom with the hand.

In addition, each of the medical condom modules may include: the wrapper; and the medical condom having a support portion that is accommodated inside the wrapper, is made of a hard material, and has a through-hole configured to allow a probe body of the medical probe to pass therethrough, and a cover portion that extends from an inner circumference of the support portion, is made of an elastically deformable material, and is configured to be put on the probe body.

According to another aspect of the present disclosure, there is provided a medical condom including: a support portion made of a hard material and having a through-hole centrally formed therein; and a cover portion connected to and extending from an inner circumference of the support portion, made of an elastically deformable material, and configured to be put on a probe body of a medical probe for obstetrics and gynecology.

With this configuration, the wrapper may be easily and automatically removed while automatically supplying the medical condom module.

Here, the support portion may have a constant thickness between the inner circumference thereof to which the cover portion is connected and an outer circumference thereof.

With this configuration, the medical condom may be moved in a state where only the support portion is supported, so that the medical condom may be prevented from being contaminated due to contact between the cover portion and surrounding structures.

In addition, the cover portion may be made of a material different from that of the support portion.

With this configuration, the medical condom may be held in a stable posture so that the support portion is not deformed, and when the medical probe is coupled with the cover portion in a held state of the medical condom, the medical condom may stably support and withstand a coupling force.

According to a medical condom and an automatic medical condom supply device according to the present disclosure, the medical condom can be supplied by automatically removing a wrapper without a user peeling off the wrapper while holding the medical condom with the hand.

Therefore, when the medical condom is coupled with the medical probe, it is possible to prevent the medical condom from being contaminated as it is held by hand, thereby preventing a patient from being infected by the contaminated medical condom during ultrasound examination.

In addition, since the user does not have to directly hold the medical condom with the hand, it is possible to prevent a lubricant or the like coated on the surface of the medical condom from being smeared on the hand.

DETAILED DESCRIPTION

Figure 1:
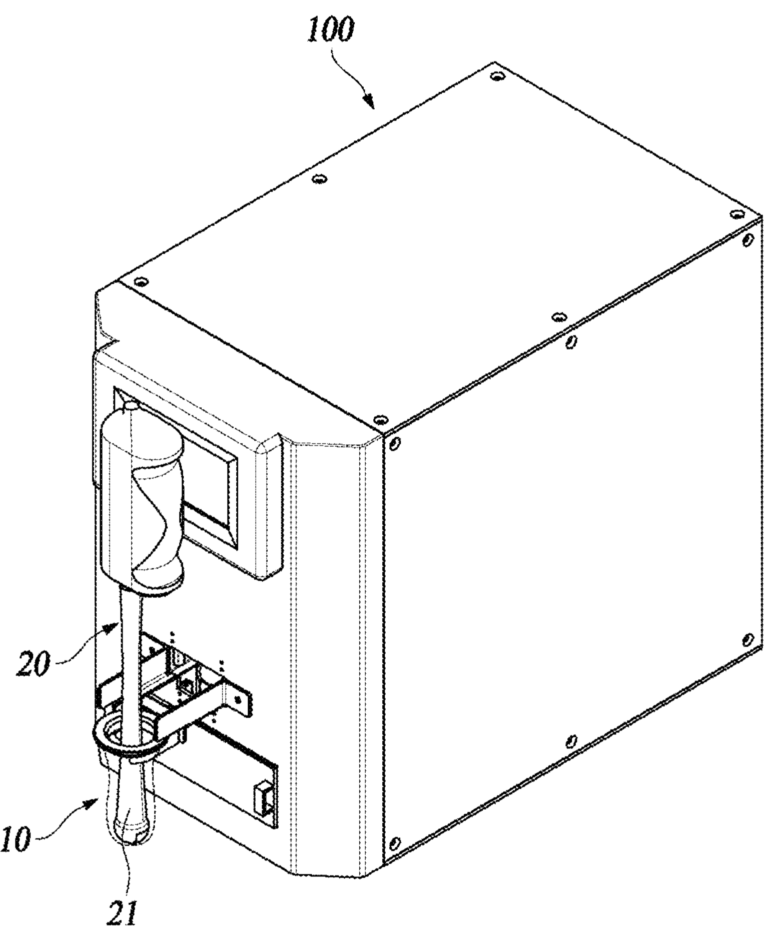
FIG. 1 is a perspective view illustrating an automatic medical condom supply device according to an embodiment of the present disclosure.
Figure 2:
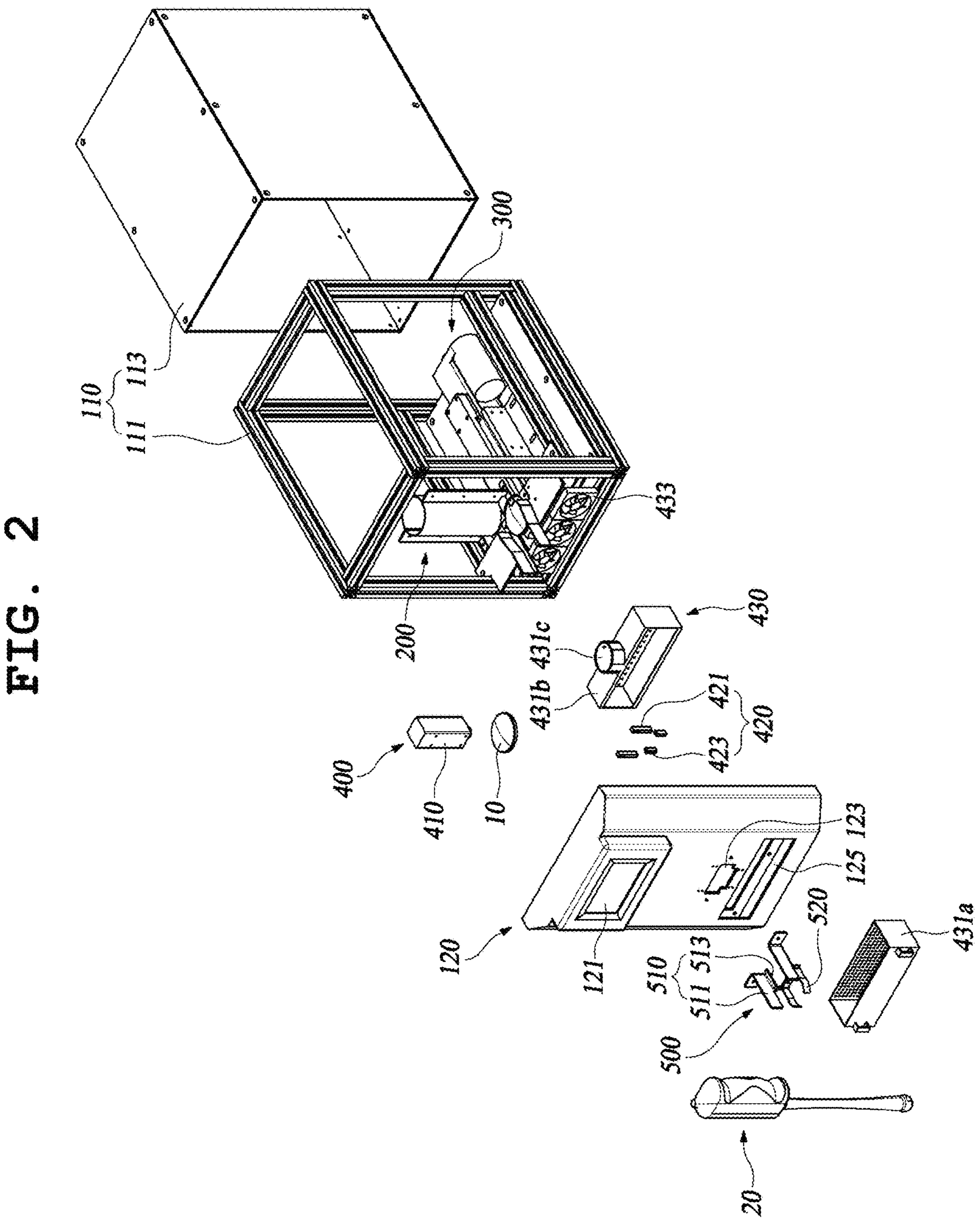
FIGS. 2 and 3 are exploded perspective views illustrating the automatic medical condom supply device illustrated in FIG. 1.
Figure 3:
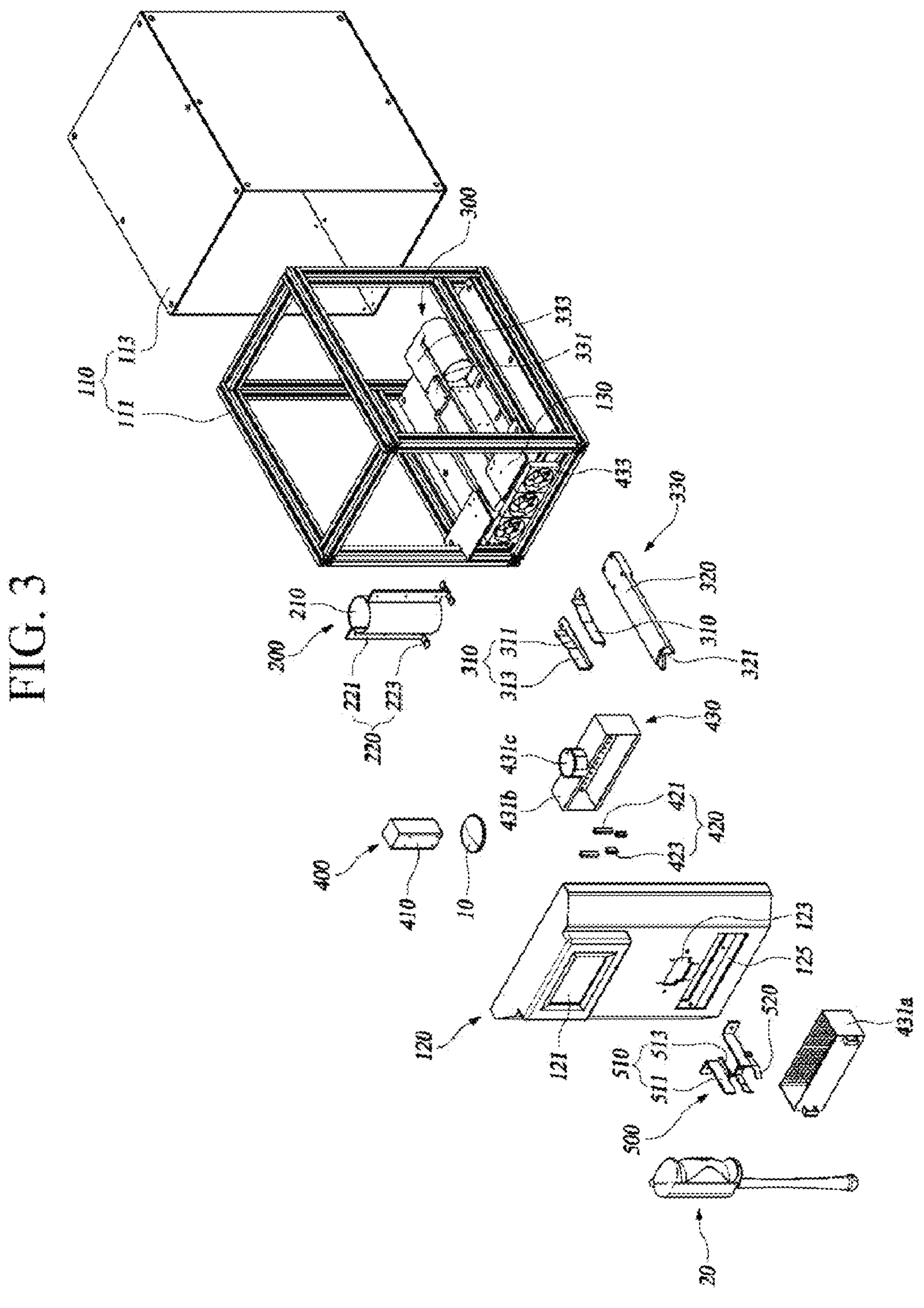

Hereinafter, a medical condom and an automatic medical condom supply device according to an embodiment of the present disclosure will be described in detail with reference to the accompanying drawings.

Referring to FIGS. 1 to 12, the automatic medical condom supply device according to the embodiment of the present disclosure includes: a device body 100; a condom supply part 200 installed inside the device body 100 to supply, one by one, medical condom modules 10 that are accommodated therein and each of which is wrapped in a wrapper 1; a condom withdrawal part 300 for moving, to the outside of the device body 100, each of the medical condom modules 10 supplied from the condom supply part 200; a wrapper removal part 400 for removing the wrapper 11 of the medical condom module 10 withdrawn to the outside of the device body 100 by the condom withdrawal part 300; and a condom holding part 500 installed outside the device body 100 to hold a medical condom 13 from which the wrapper 11 has been removed.

Figure 4:
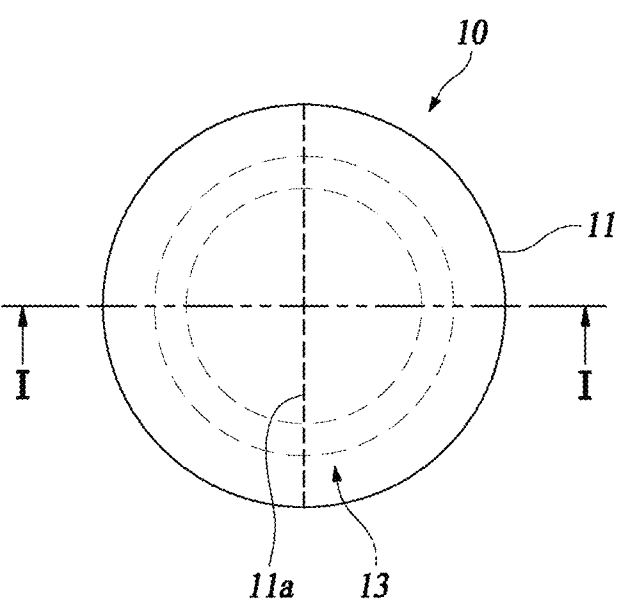
FIG. 4 is a plan view illustrating a medical condom module including a medical condom according to an embodiment of the present disclosure.
Figure 5:
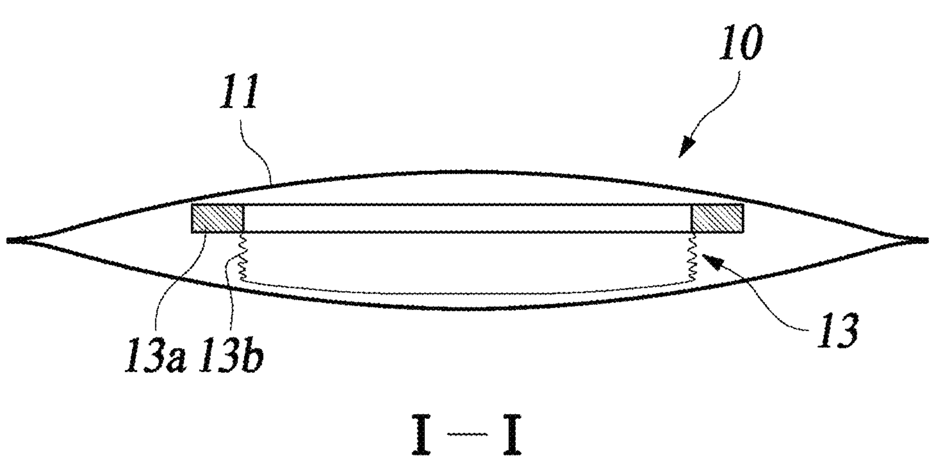
FIG. 5 is a sectional view taken along line I-I of FIG. 2.
Figure 6:
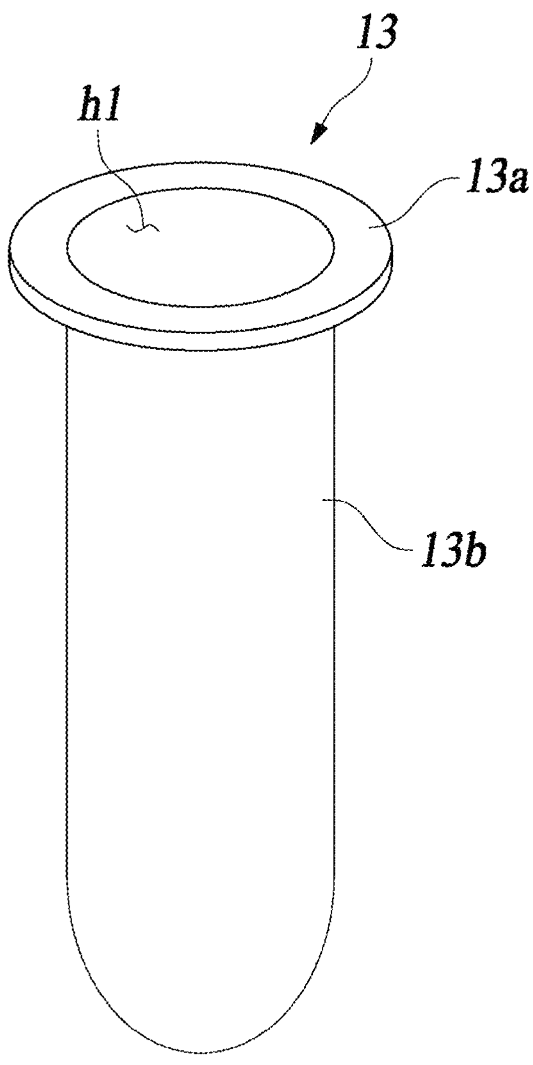
FIG. 6 is a perspective view illustrating a medical condom according to an embodiment of the present disclosure.
Figure 7:
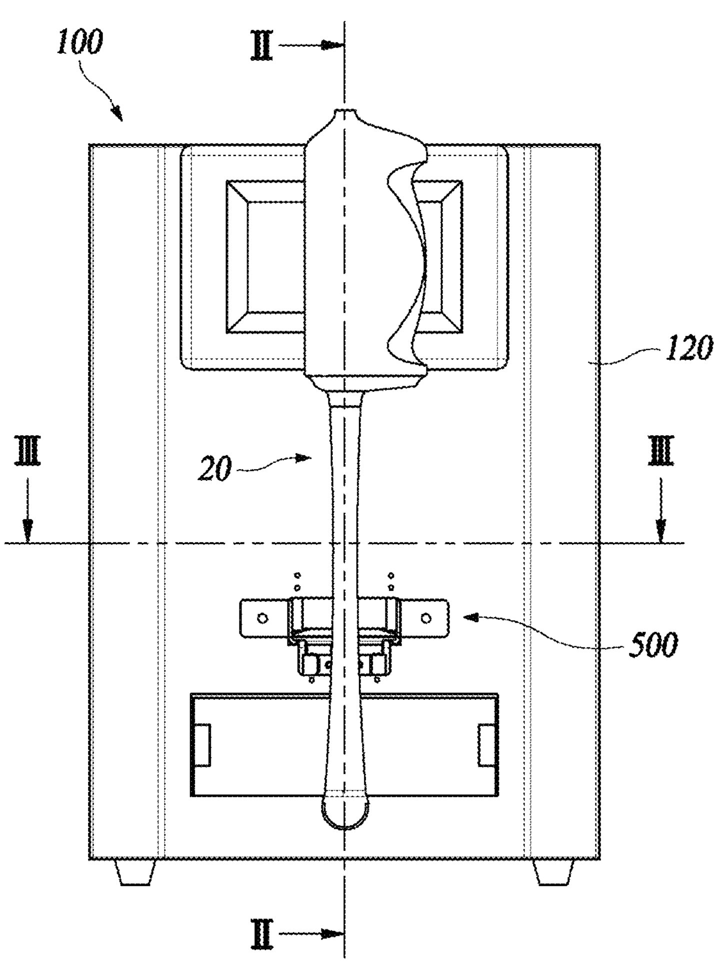
FIG. 7 is a front view illustrating the automatic medical condom supply device illustrated in FIG. 1.
Figure 8:
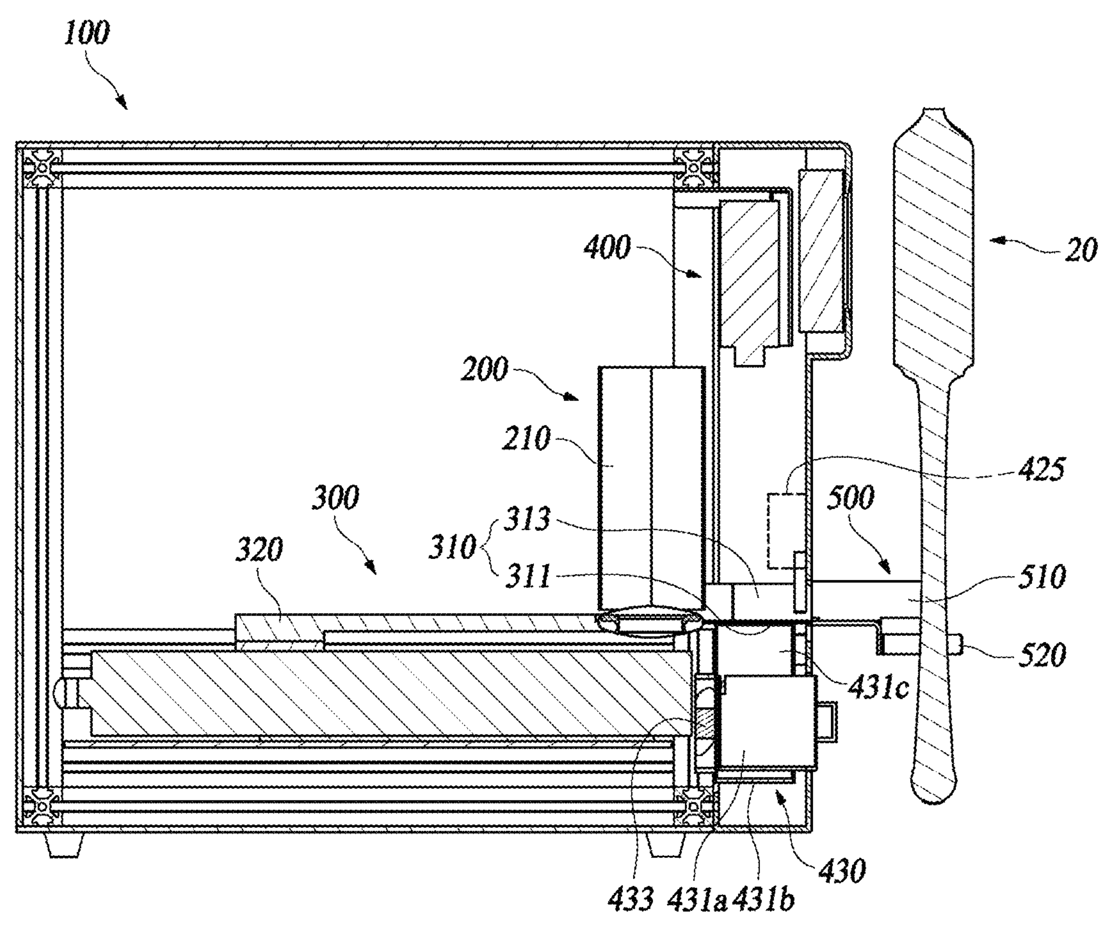
FIG. 8 is a sectional view taken along line II-II of FIG. 7.
Figure 9:
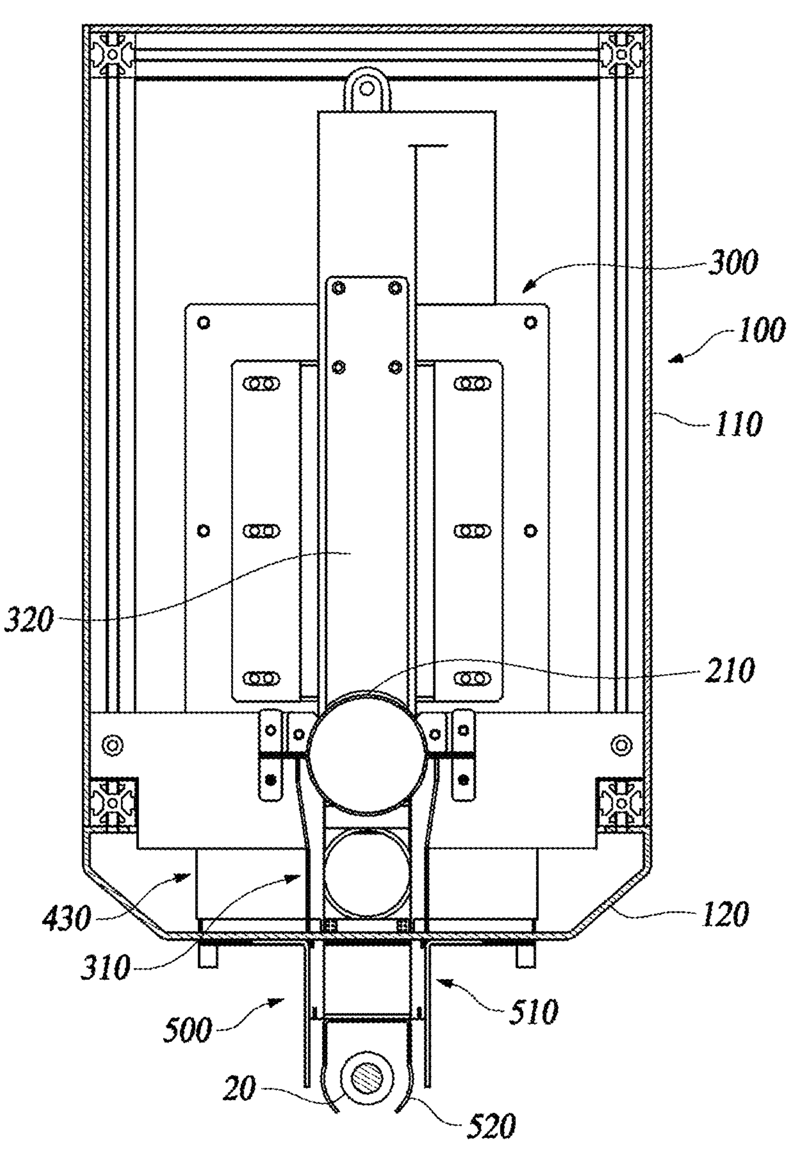
FIG. 9 is a sectional view taken along line III-III of FIG. 7.

Here, as illustrated in FIGS. 4 to 6, each of the medical condom modules 10 includes the wrapper 11 and the medical condom 13 accommodated inside the wrapper 11. The wrapper 11 is made of a material such as vinyl or synthetic resin, and stores the medical condom 13 in an airtight state so as not to be exposed to the outside. The wrapper 11 may be cut by a laser or the like.

The medical condom 13 includes a support portion 13*a* and a cover portion 13*b* connected to the support portion 13*a*. The support portion 13*a* may be made of a hard material such as synthetic resin so as not to be deformed by an external force, or a cushion material (silicone, synthetic rubber, etc.) having a thickness that is not easily deformed by an external force. Of course, in some cases, the support portion 13*a* may be made of a metal material. The support portion 13*a* has a ring shape, and has a through-hole hl centrally formed therein. The support portion 13*a* has a constant width and thickness, and has a plate-shaped ring structure with an inner circumference and an outer circumference. Here, a width between the inner and outer circumferences of the support portion 13*a* does not change and is maintained at a fixed value. That is, even when the cover portion 13*b* is put on a probe body 21 of a medical probe 20, the width of the support portion 13*a* does not change.

The cover portion 13*b* may be made of a soft material such as vinyl, synthetic resin, or silicon, and is used to cover the probe body 21 of the probe 20. The cover portion 13*b* has an open first end connected to the support portion 13*a* and a second end closed and accommodated inside the wrapper 11 in an overlapped state. The cover portion 13*b* may be made of the same material as conventional medical condoms.

The automatic medical condom supply device according to the present disclosure is used to automatically put the medical condom module 10 having the above configuration on the probe body 21 of the medical probe 20.

The device body 100 has a casing structure having a space therein, and has a main body 110 with an open front, and a front cover 120 coupled to the front of the main body 110. The main body 110 may have a main frame 111 and a main body casing 113 coupled to the main frame 111 to surround an outer circumference thereof. Here, the main frame 111 may be selectively applied.

The front cover 120 is coupled to the open front of the main body 110, and is preferably installed to be openable. The front cover 120 is preferably provided with a panel 121 for displaying an operating state of the device and manipulating the operation of the device. The panel 121 may include a touch screen. In addition, the front cover 120 has an outlet 123 through which the medical condom 13 from which the wrapper 11 has been removed is exposed.

The condom supply part 200 includes a supply hopper 210 installed inside the device body 110 and a hopper support bracket 220 for fixing and supporting the supply hopper 210 inside the device body 110. The supply hopper 210 has a tubular structure with open top and bottom, and accommodates the condom modules 10 stacked therein. The condom modules 10 accommodated in the supply hopper 210 are sequentially dropped and supplied in order from the lowermost condom module 10, and the dropped condom module 10 is seated on a guide member 310, which will be described later.

A pair of hopper support brackets 220 are coupled to an outer surface of the supply hopper 210 at symmetrical positions. Each of the hopper support brackets 220 includes a support bracket body 221 coupled to the outer surface of the supply hopper 210, and a support portion 223 protruding from a lower end of the support bracket body 221 to support the supply hopper 210 to be spaced apart from the guide member 310. The support portion 223 is coupled to and fixed to a fixing bracket 130 installed inside the device body 110.

Here, a pair of fixing brackets 130 are horizontally installed at the same height and are spaced apart from each other. Therefore, the guide member 310 faces the supply hopper 210 between the pair of fixing brackets 130 while being spaced apart from the supply hopper 210. It is preferable that the distance (height) between the supply hopper 210 and the guide members 310 corresponds to the thickness of each of the condom modules 10. Therefore, the lowermost condom module 10 in the supply hopper 210 is discharged from the supply hopper 210 and loaded while being seated on the guide member 310. The condom module 10 in the loaded state passes through a wrapper removal position for removing the wrapper by the condom withdrawal part 300. As the wrapper is removed, only the medical condom 13 is discharged to the condom holding part 500 through the outlet 123.

Here, in addition to the configuration of the condom supply part 200, various configurations capable of supplying the condom modules 10 one by one are possible, and the present disclosure is not limited by the configuration of the condom supply part 200 as described above.

The condom withdrawal part 300 includes the guide member 310 installed inside the main body 110, a transfer member 320 for withdrawing the condom module 10 loaded on the guide member 310 out of the outlet 123 via the wrapper removal position B, and a transfer member driver 330 for reciprocally driving the transfer member 320.

A pair of guide members 310 are installed to be spaced apart from each other symmetrically with respect to a withdrawal direction of the condom modules 10. Each of the guide members 310 includes a bottom guide portion 311, and a side guide portion 313 bent at an edge of the bottom guide portion 311. The guide members 310 extends from a position below the supply hopper 210 to the outlet 123, and guides the condom module 10 supplied from the supply hopper 210 to the outlet 123. The guide members 310 are supported and fixed to the fixing brackets 130. The condom module 10 is loaded with an edge thereof being seated on the respective bottom guide portions 311 of the pair of guide members 310 having the above configuration, and moved toward the outlet 123 by the transfer member 320.

Of course, the pair of guide members 310 may be integrally formed. That is, the pair of guide members 310 may have a structure in which at least one of first ends or second ends of the guide members 310 are connected to each other with a slit centrally formed therebetween so that the removed wrapper is dropped through the slit and collected by the wrapper collection part.

The transfer member 320 is installed to reciprocate horizontally inside the main body 110. In detail, a push member driven reciprocally by the transfer member driver 330 may be provided so that a contact pressure portion 321 at a front end of the transfer member 320 pushes the condom module 10 loaded on the guide members 310 out of the outlet 123. The transfer member 320 preferably has a plate structure with a predetermined length, and has a thickness smaller than the distance between the guide members 310 and the supply hopper 210. It is preferable that the transfer member 320 is installed so that an upper surface thereof is positioned at the same height as a bottom outlet of the supply hopper 210. Thus, when the transfer member 320 pushes and withdraws the lowermost condom module 10 in the supply hopper 210, the transfer member 320 blocks the outlet of the supply hopper 210. Then, when the transfer member 320 returns to an initial position, the outlet of the supply hopper 210 is opened and the condom module 10 is dropped and discharged.

The transfer member driver 330 is installed inside the main body 110 to drive the transfer member 320 reciprocally. The transfer member driver 330 includes a moving portion 331 to which the transfer member 320 is coupled, and a driving portion 333 for reciprocally driving the moving portion 331. The driving portion 333 moves the moving portion 331 to a desired position at a desired speed, and may include various known driving means such as a linear motor, a hydraulic cylinder, and a lead screw. That is, various known driving means for reciprocating the transfer member 320 may be applied, and the present disclosure is not limited by a specific driving means.

The wrapper removal part 400 removes the wrapper 11 of the condom module 10 before the condom module 10 is moved by the transfer member 320 and withdrawn through the outlet 123. The wrapper removal part 400 includes a laser generation module 410 installed inside the device body 100 to partially cut the wrapper 11 of the condom module 10 using a laser, and a wrapper clamping member 420 installed on a movement path of the condom module 10 to forcibly peel off the wrapper 11 partially cut by the laser generation module 410.

Figure 10:
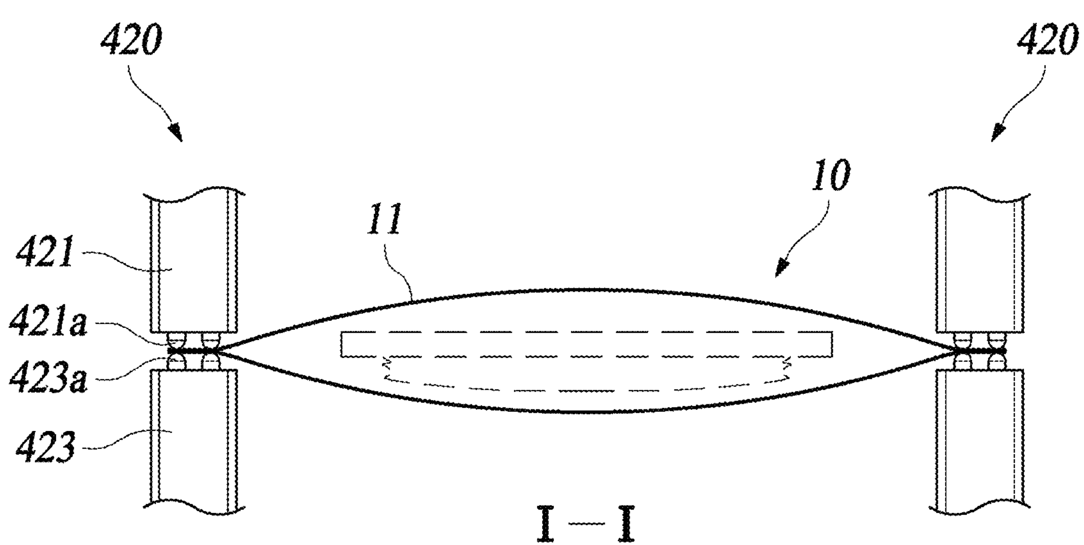
FIG. 10 is a view illustrating the process of removing a wrapper of the condom module.
Figure 11:
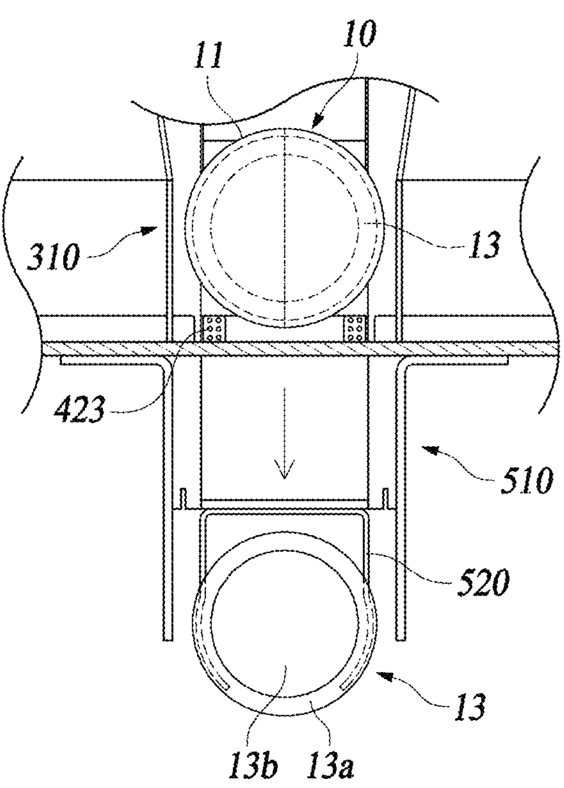
FIG. 11 is a view illustrating a state in which the medical condom is separated from the wrapper and moved to a condom holding part.

The laser generation module 410 is installed inside the main body 110, and is preferably disposed above the movement path of the condom module 10 pushed and moved by the transfer member 320. Thus, when the condom module 10 is moved toward the outlet 123 by the transfer member 320 and reaches a position corresponding to the laser generation module 410, the laser generation module 410 is driven to emit the laser to form an incision 11*a* (see FIG. 4) in the wrapper 11 of the condom module 10. The condom module 10 having the incision 11*a* is moved toward the outlet 123 by the transfer member 320 and interferes with the wrapper clamping member 420, so that the incision 11*a* is opened and the medical condom 13 is separated and taken out from the wrapper 11. A pair of wrapper clamping members 420 are disposed symmetrically on opposite sides of the outlet 123. Each of the wrapper clamping members 420 includes upper and lower clamping members 421 and 423 installed to be spaced apart from each other. It is preferable that the upper and lower clamping members 421 and 423 are disposed at a distance smaller than the thickness of the edge of the condom module 10 in a state where the medical condom 13 is accommodated inside the wrapper 11. In addition, as illustrated in FIG. 10, it is preferable that the upper and lower clamping members 421 and 423 have friction protrusions 421*a* and 423*a*, respectively, on wrapper clamping surfaces thereof to increase a frictional force and effectively clamp the wrapper 11. In addition, the pair of wrapper clamping members 420 are disposed at a distance larger than the size of the medical condom 13 and smaller than the size of the wrapper 11 so that the medical condom 13 is pushed out of the wrapper 11 by the transfer member 320 and discharged through the outlet 123 in a state where opposite sides of the edge of the wrapper 11 are clamped, and the wrapper 11 is collected separately by the wrapper collection part 430.

In addition, it is more preferable that the upper and lower clamping members 421 and 423 are installed to be moved close to or away from each other. In this case, at least one of the upper and lower clamping members 421 and 423 is moved up and down by a lifting means 425 to strongly clamp the edge of the wrapper 11, so that the wrapper 11 is peeled off more effectively. The lifting means 425 may include an actuator such as a hydraulic cylinder.

The wrapper collection part 430 collects the wrapper 11 peeled off and separated from the medical condom 13. The wrapper collection part 430 includes a wrapper collection chamber 431 installed inside the main body 110 to collect the wrapper, and a suction fan 433 for providing a suction force to the wrapper collection chamber 431.

The wrapper collection chamber 431 includes a wrapper collection container 431*a*, and a mounting chamber 431*b* in which the wrapper collection container 431*a* is detachably mounted and having a wrapper suction port 431*c*. The wrapper collection container 431*a* is attached to and detached from the mounting chamber 431*b* inside the device body 100 through a collection container mounting hole 125 of the front cover 120. The wrapper collection container 431*a* has a basket structure with an open top, and may have a plurality of ventilation holes formed on a surface thereof in contact with a rear surface of the mounting chamber 431*b*.

The mounting chamber 431*b* is fixedly installed at the bottom of the inside of the main body 110, and is preferably installed corresponding to a position where the wrapper 11 is peeled off. The mounting chamber 431*b* has an open front facing the collection container mounting hole 125 so that the wrapper collection container 131 is mounted therein through the open front. The mounting chamber 431*b* has a plurality of ventilation holes formed on a rear surface thereof so that the suction force generated by the suction fan 433 is transmitted to the wrapper suction port 431*c* via the wrapper collection container 431. The wrapper suction port 431*c* is positioned correspondingly below the upper and lower clamping members 421 and 423 so that the wrapper 11 separated from the medical condom 13 is sucked into the wrapper suction port 431*c* by the suction force and effectively collected in the wrapper collection container 431*a*.

The condom holding part 500 is installed on a front surface of the device body 100, i.e., around the outlet 123 of the front cover 120. The condom holding part 500 includes a guide bracket 510, and a condom support member 520 installed at a front end of the guide bracket 510 to support the medical condom 13. The guide bracket 510 includes a pair of side guiders 511 fixed to the front cover 120, and a bottom guider 513 extending horizontally from a lower end of each of the side guiders 511. The medical condom 13 pushed out by the transfer member 320 through the outlet 123 is stably moved along the side guiders 511 with the support portion 13*a* being supported by the respective bottom guiders 513, and is supported by the support member 520.

The condom support member 520 is installed at the front end of the guide bracket 510, is preferably connected to the front end of the guide bracket 510 to be located at a lower position than the bottom guiders 513 of the guide bracket 510. A pair of condom support members 520 are disposed to be spaced apart from each other to support only the support portion 13*a* of the medical condom 13, so that the medical condom 13 is supplied in a state where the cover portion 13*b* is not in contact with surrounding structures.

When the medical condom 13 is mounted on the condom support members 520, as illustrated in FIG. 1, a user brings the probe body 21 close to the medical condom 13 while holding the probe 20 so that the cover portion 13*b* is put on the probe body 21.

As described above, according to the medical condom module and the automatic medical condom supply device according to the embodiment of the present disclosure, the structure of the medical condom 13 is composed of the support portion 13*a* and the cover portion 13*b*. With this configuration, it is easy to move the medical condom 13 while removing the wrapper 11. In particular, the medical condom 13 is supplied to be held through the support portion 13*b* while preventing contact of the cover portion 13*b*, so that the medical condom 13 is easily coupled with the probe body 21 of the probe 20.

In addition, each of the condom modules 10 is supplied individually from the supply hopper 210, and the wrapper 11 is separated from the medical condom 13 by automatically removing the wrapper 11 while moving the supplied condom module 10 to the outlet 123 of the device body 100. Therefore, it is possible to solve the problem of the related art in which the user has to peel off the wrapper 11 with the hand and put the medical condom 13 on the medical probe while holding the medical condom 13 with the hand, thereby preventing contamination of the medical condom 13.

The removed wrapper 11 is collected separately, thereby preventing contamination inside the device body 100.

Figure 12:
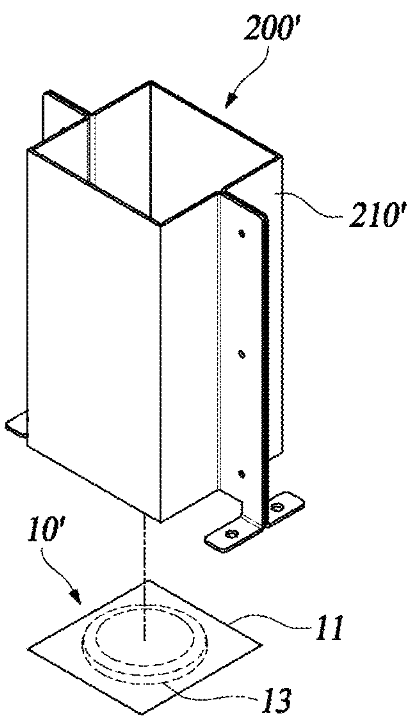
FIG. 12 is a schematic perspective view illustrating another example of a condom supply part and a medical condom module illustrated in FIG. 3.

Although it has been described above that the wrapper 11 of the condom module 10 has a circular shape, this is only exemplary. That is, as illustrated in FIG. 12, a medical condom module 10' in which a wrapper 11' is formed in a rectangular shape may be applied. In this case, a condom supply part 200' for supplying the condom module 10' includes a supply hopper 210' formed in a rectangular tubular shape. As such, it is preferable that the shape of the supply hopper 210' corresponds to the shape of the wrapper 11' of the condom module 10'. Therefore, wrappers and supply hoppers of various condom modules 10 can be manufactured in various shapes, and the present disclosure is not limited by a specific shape.

Also, although it has been described above that the support portion 13*a* of the medical condom 13 has a ring shape and the through-hole hl thereof has a circular shape, this is only exemplary. That is, the shape of the probe body of the medical probe may be a rod as illustrated in the drawings, but various other shapes are possible. Therefore, it is obvious that the shape of the medical condom and the shapes of the support portion 13*a* and the through-hole hl can be variously applied so that the medical condom is put on the probe body corresponding to the shape thereof.

Although a specific embodiment of the present disclosure has been described and illustrated as described above, it will be understood by those skilled in the art to which the present disclosure pertains that the present disclosure is not limited to the described embodiment but may be variously changed and modified without departing from the spirit and scope of the present disclosure. Accordingly, the changes and modifications should not be individually understood from the technical spirit and aspects of the present disclosure and the modified embodiments fall within the scopes of the claims of the present disclosure.

What is claimed is:

1. An automatic medical condom supply device comprising:

a device body;

a condom supply part installed inside the device body and configured to supply, one by one, medical condom modules including a medical condom and a wrapper, each of the medical condom is wrapped in the wrapper;

a condom withdrawal part configured to move, to an outside of the device body, through an outlet formed in the device body, each of the medical condom modules supplied from the condom supply part;

a wrapper removal part configured to remove the wrapper of the medical condom module withdrawn to the outside of the device body by the condom withdrawal part; and a condom holding part installed outside the device body and configured to hold the medical condom discharged through the outlet, and a medical probe is coupled with the medical condom after the wrapper has been removed, wherein each of the medical condom modules comprises:

the wrapper; and the medical condom including a support portion accommodated inside the wrapper and formed of a hard material, the support portion having a through-hole configured to allow a probe body of the medical probe to pass therethrough, and a cover portion extending from an inner circumference of the support portion, the cover portion being made of an elastically deformable material and configured to be put on the probe body, wherein the condom holding part comprises:

a guide bracket installed outside the outlet of the device body and configured to support an edge of the medical condom discharged through the outlet and guide movement of the medical condom; and a condom support member installed at a front end of the guide bracket and configured to support the support portion located at an edge of the medical condom such that a width between the inner circumference and an outer circumference of the support portion is fixed, thereby allowing the medical probe to be coupled with the medical condom.

2. The automatic medical condom supply device of claim 1, wherein the condom withdrawal part comprises:

a guide member installed inside the device body and configured to guide the condom module supplied from the condom supply part to be moved toward the outlet;

a transfer member configured to withdraw the condom module loaded on the guide member out of the outlet via a wrapper removal position; and a transfer member driver includes a driving means to reciprocally drive the transfer member.

3. The automatic medical condom supply device of claim 2, wherein the guide member comprises:

a bottom guide portion configured to support the condom module to be slidably moved in a seated state on the bottom guide portion; and a side guide portion formed by bending at an edge of the bottom guide portion.

4. The automatic medical condom supply device of claim 2, wherein the transfer member comprises a push member installed inside the device body to be reciprocally movable, and configured to be moved while pushing the condom module supplied from the condom supply part and loaded on the guide member out of the outlet via the wrapper removal position by the wrapper removal part.

5. The automatic medical condom supply device of claim 1, wherein the wrapper removal part comprises:

a laser generation module installed inside the device body and configured to partially cut the wrapper of the condom module using a laser; and a wrapper clamping member installed on a movement path of the condom module and configured to forcibly peel off the wrapper partially cut by the laser generation module.

6. The automatic medical condom supply device of claim 5, wherein the wrapper clamping member comprises a pair of wrapper clamping members that are symmetrically disposed on opposite sides of the outlet, and wherein each of the pair of wrapper clamping members comprises upper and lower clamping members vertically installed to face each other and be spaced apart from each other and configured to vertically interfere with an edge of the wrapper of the condom module to separate the wrapper from the medical condom moved through the outlet.

7. The automatic medical condom supply device of claim 6, wherein each of the upper and lower clamping members has a friction protrusion on an end portion thereof that interferes with the wrapper.

8. The automatic medical condom supply device of claim 6, wherein at least one of the upper and lower clamping members is installed to be reciprocally movable.

9. The automatic medical condom supply device of claim 1, wherein the support portion has a constant thickness between the inner circumference from which the cover portion is connected and an outer circumference thereof.

10. A medical condom comprising:

a support portion made of a hard material and having a through-hole centrally formed therein; and a cover portion connected to and extending from an inner circumference of the support portion, made of an elastically deformable material, and configured to be put on a probe body of a medical probe for obstetrics and gynecology, wherein the medical condom is wrapped in a wrapper to form a medical condom module, and the medical condom module is supplied through an automatic medical condom supply device that comprises:

a device body;

a condom supply part installed inside the device body and configured to supply, one by one, the medical condom modules;

a condom withdrawal part configured to move, to an outside of the device body, through an outlet formed in the device body, each of the medical condom modules supplied from the condom supply part;

a wrapper removal part configured to remove the wrapper of the medical condom module withdrawn to the outside of the device body by the condom withdrawal part;

a guide bracket installed outside an outlet of the device body and configured to support an edge of the medical condom discharged through the outlet and guide movement of the medical condom; and a condom support member installed at a front end of the guide bracket and configured to support the support portion located at the edge of the medical condom such that a width between the inner circumference and an outer circumference of the support portion is fixed, thereby allowing a medical probe to be coupled with the medical condom.

11. The medical condom of claim 10, wherein the support portion has a constant thickness between the inner circumference from which the cover portion is connected and an outer circumference thereof.

12. The medical condom of claim 10, wherein the cover portion is made of a material different from that of the support portion.

* * * * *